United States Patent [19]

Camaggi et al.

[11] Patent Number: 5,401,763
[45] Date of Patent: Mar. 28, 1995

[54] DERIVATIVES OF ARYLACETIC ESTERS DISPLAYING HIGH FUNGICIDAL ACTIVITY

[75] Inventors: Giovanni Camaggi, Novara; Lucio Filippini, San Donato Milanese; Raul Riva, Novara; Isabella Venturini, Milan; Giampaolo Zanardi, Vigevano; Carlo Garavaglia, Cuggiono; Ernesto Signorini, Malnate; Mario Ferri, Milan, all of Italy

[73] Assignee: Ministero Dell 'Universita' e Della Ricerca Scientifica e Technologica, Rome, Italy

[21] Appl. No.: 191,783

[22] Filed: Feb. 3, 1994

[30] Foreign Application Priority Data

Feb. 5, 1993 [IT] Italy .................. MI93A0195

[51] Int. Cl.$^6$ .............. A61K 31/42; C07D 261/04; C07D 213/16; C07D 239/26
[52] U.S. Cl. ................ 514/378; 514/380; 514/340; 514/256; 514/252; 514/269; 548/240; 548/243; 546/275; 544/296; 544/298; 544/315; 544/333; 544/334; 544/335; 544/224; 544/238; 544/239
[58] Field of Search ............ 548/240, 243; 514/378, 514/380, 340, 256, 269, 252; 546/275; 544/296, 298, 315, 333, 334, 335, 224, 238, 239

[56] References Cited

U.S. PATENT DOCUMENTS

| | | | |
|---|---|---|---|
| 5,166,216 | 11/1992 | Schuetz et al. | 514/406 |
| 5,250,553 | 10/1993 | Schuetz et al. | 514/378 |
| 5,254,717 | 10/1993 | Grammenos et al. | 560/35 |
| 5,294,628 | 3/1994 | Schuetz et al. | 514/364 |

FOREIGN PATENT DOCUMENTS

| | | | |
|---|---|---|---|
| 0256667 | 2/1988 | European Pat. Off. | 514/378 |
| 0499823 | 1/1993 | European Pat. Off. | 560/35 |
| 90/07493 | 7/1990 | WIPO | 514/378 |

OTHER PUBLICATIONS

"Copper(I)-Promoted Coupling Reaction of Aryl Halided With Sodium", Chemistry Letters, The Chemistry Society of Japan, 1981.

Primary Examiner—Mary C. Lee
Assistant Examiner—Joseph K. McKane
Attorney, Agent, or Firm—George P. Hoare, Jr.

[57] ABSTRACT

Arylacetic ester derivative-based compounds having the general formula (I):

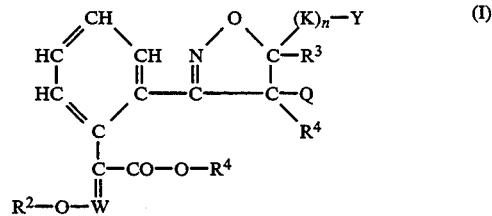

28 Claims, No Drawings

DERIVATIVES OF ARYLACETIC ESTERS DISPLAYING HIGH FUNGICIDAL ACTIVITY

The present invention relates to compounds based on derivatives of arylacetic esters.

More particularly, the present invention relates to arylacetic ester derivative-based compounds displaying high antifungal activity, to a process for preparing them and to their use in the agricultural field, as fungicides.

Therefore, the object of the present invention are compounds based on derivatives of arylacetic esters having the general formula (I):

$$\text{(I)}$$

in which:

$R^1$ and $R^2$, which may be the same or different from each other, are an either linear or branched $C_1$–$C_6$ alkyl or haloalkyl group;

$R^3$ and $R^4$, which may be the same or different from each other, represent a hydrogen atom, a $C_1$–$C_2$ alkyl group, a $COOR^5$ group in which $R^5$ represents an either linear or branched $C_1$–$C_6$ alkyl group, a cyano group, or, taken together, constitute a bond;

W represents a nitrogen atom, or the $$=\underset{|}{C}-H$$

group;

Y and Q, which may be the same or different from each other, represent a nitrile group, an either linear or branched $C_1$–$C_6$ alkyl or carboalkoxy group, a phenyl group, a heterocyclic $C_5$–$C_{10}$ group in which the heteroatoms are selected from oxygen, nitrogen or sulfur, wherein said phenyl, heterocyclic, linear or branched $C_1$–$C_6$ alkyl or alkoxy groups may also be optionally substituted with:

halogens, such as chloro, fluoro, bromo, iodo;
linear or branched $C_1$–$C_6$ alkyl or haloalkyl groups;
linear or branched $C_1$–$C_6$ alkoxy or haloalkoxy groups;
a nitrile group;
an either linear or branched $C_2$–$C_8$ carboxyalkyl group;

a —(V)$_m$—Z group, in which Z stands for:

an either linear or branched $C_1$–$C_6$ alkyl group, a phenyl group, a heterocyclic $C_5$–$C_{10}$ group in which the heteroatoms are selected from oxygen, nitrogen or sulfur, wherein said phenyl, heterocyclic, linear or branched $C_1$–$C_6$ alkyl groups may also be optionally substituted with:
halogens, such as chloro, fluoro, bromo, iodo;
linear or branched $C_1$–$C_6$ alkyl or haloalkyl groups;
linear or branched $C_1$–$C_6$ alkoxy or haloalkoxy groups;
a nitrile group;
an either linear or branched $C_2$–$C_8$ carboxyalkyl group;

K and V, which may be the same or different from each other, represent an oxygen or sulfur atom, or a carbonyl group;

n and m, which may be the same or different from each other, are zero, or 1.

The structure of general formula (I) can display at least one centre of isomerism of (E)/(Z) type.

The compounds of general formula (I) are antifungal agents for agricultural purposes.

Examples of $R^1$ and $R^2$ radicals are: methyl, ethyl, trifluoromethyl, 1,1,2,2-tetrafluoroethyl, and so forth.

Examples of $R^3$ and $R^4$ radicals are: methyl, ethyl, carbomethoxy, carboethoxy, carboisopropoxy, and so forth.

Examples of Y, Q and Z radicals are: methyl, ethyl, isopropyl, tert.-butyl, trifluoromethyl, perfluoroethyl, 1,1,2,2-tetrafluoroethyl, phenyl, 2-chlorophenyl, 3-chlorophenyl, 4-chlorophenyl, 2,4-dichlorophenyl, 4-fluorophenyl, 3-methoxyphenyl, 3-trifluoromethylphenyl, 4-trifluoromethylphenyl, 3-trifluoromethoxyphenyl, 2-cyanophenyl, 4-cyanomethyl, 2-carbomethoxyphenyl, pyridyl, 3-cyanopyridyl, 4-cyanopyridyl, 3-carbomethoxypyridyl, 3,5-dichloropyridyl, pyrimidyl, 4-methylpyrimidyl, 2-trifluoromethylpyrimidyl, 4-trifluoromethylpyrimidyl, pyradizinyl, 2-trifluoro-methylpyradizinyl, 5-methylthienyl, 5-trifluoromethyl-thienyl, 4-methyl-5-trifluoromethylthiazolyl, 5-tert.-butyl-thiazolyl, 5-chlorobenzothiazolyl, and so forth.

Compounds of general formula (I) not illustrated in the examples, but equally interesting owing to their fungicidal activity, are:

* (Z)-methyl 3-methoxy-2-{2-[5-(2,4-dichlorophenyl)isooxazol-3-yl]phenyl}acrylate;
* (Z)-methyl 3-methoxy-2-{2-[5-(4-trifluoromethylphenyl)isooxazol-3-yl]phenyl}acrylate;
* (Z)-methyl 3-methoxy-2-{2-[5-(4-chlorobenzoyl-phenyl)isooxazol-3-yl]phenyl}acrylate;
* (Z)-methyl 3-methoxy-2-{2-[5-(4-chlorophenoxy-phenyl)isooxazol-3-yl]phenyl}acrylate;
* (Z)-methyl 3-methoxy-2-{2-[5-(4-chlorobenzoyl)isooxazol-3-yl]phenyl}acrylate;
* (Z)-methyl 3-methoxy-2-{2-[5-(4-pyrimidyl-2-oxybenzoyl)isooxazol-3-yl]phenyl}acrylate;
* (Z)-methyl 3-methoxy-2-{2-[5-(6-phenoxy-3-trifluoromethylpyridyl-2-oxy)isooxazol-3-yl]phenyl}acrylate;
* (Z)-methyl 3-methoxy-2-{2-[5-(6-(2-cyanophenoxy)pyrimidin-4-yloxy)isooxazol-3-yl]phenyl}acrylate;
* (Z)-methyl 3-methoxy-2-{2-[5-(6-(4-chlorophenoxy)pyrimidin-4-yl)isooxazol-3-yl]phenyl}acrylate;
* (Z)-methyl 3-methoxy-2-{2-[5-(3-(3-cyano-5-chloropyridyl-2-oxy)phenyl)isooxazol-3-yl]phenyl}acrylate;
* (Z)-methyl 3-methoxy-2-[2-(5-cyanoisooxazol-3-yl)phenyl]acrylate;
* (Z)-methyl 3-methoxy-2-[2-(5-carbomethoxyisooxazol-3-yl)phenyl]acrylate;
* (Z)-methyl 3-methoxy-2-{2-[5-(5-(4-chlorophenyl)-4-trifluoromethylthiazol-2-yl)isooxazol-3-yl]phenyl}acrylate;
* (Z)-methyl 3-methoxy-2-[2-(5-benzothiazol-2-yl-isooxazol-3-yl]phenyl}acrylate;
* (Z)-methyl 2-methoxyimino-2-{2-[5-(2,4-dichlorophenyl)isooxazol-3-yl]phenyl}acetate;
* (Z)-methyl 2-methoxyimino-2-{2-[5-(4-trifluoromethyl)isooxazol-3-yl]phenyl}acetate;

and so forth.

The compounds of general formula (I) according to the present invention can be obtained by means of a process comprising causing an aldoxime compound having the general formula (II):

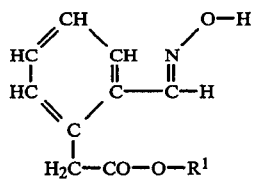
(II)

wherein $R^1$ has the same meaning as disclosed hereinabove, to react with an unsaturated compound having the general formula (III):

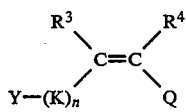
(III)

wherein $R^3$, $R^4$, Y, K and n have the same meaning as disclosed hereinabove, in the presence of a halogenating agent such as, e.g., sodium hypochlorite, chlorine or bromine, with a compound of general formula (IV) being obtained:

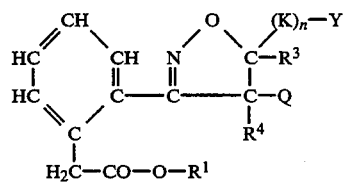
(IV)

When W represents the

group, the compound of general formula (IV) is caused to react with an alkyl formate of general formula (V):

 (V)

in which $R^6$ represents a $C_1$–$C_3$ alkyl group, in a dipolar protic or aprotic solvent such as, e.g., methyl alcohol, tert.-butyl alcohol, N,N-dimethylformamide, N-methylpyrrolidone, in the presence of a base such as, e.g., sodium hydride, potassium tert.-butoxide, at a temperature comprised within the range of from −10° C. to 80° C., with the salt of general formula (VI) being obtained:

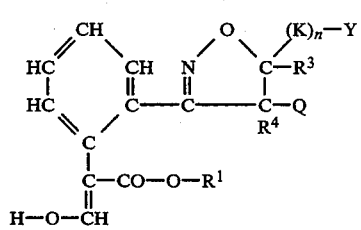
(VI)

which is subsequently caused to react with a halogenating agent $R^2$—X in which $R^2$ has the above disclosed meaning and X stands for a halogen atom, such as chlorine, bromine, iodine, or with an activated ester such as p-toluene sulfonate, at a temperature comprised within the range of from −10° C. to 80° C., with the desired compound of formula (Ia) being thus obtained:

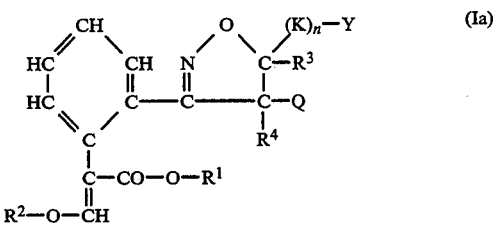
(Ia)

When W is a nitrogen atom, the compound of general formula (IV) is, on the contrary, caused to react with an organic nitrite of general formula (VII):

 (VII)

wherein $R^7$ represents a linear or branched $C_2$–$C_8$ alkyl group, in a dipolar protic or aprotic solvent such as, e.g., methyl alcohol, tetrahydrofuran, dioxane, in the presence of a base such as, e.g., sodium hydride, potassium tert.-butoxide, at a temperature comprised within the range of from −10° C. up to 80° C., with the salt of general formula (VIII):

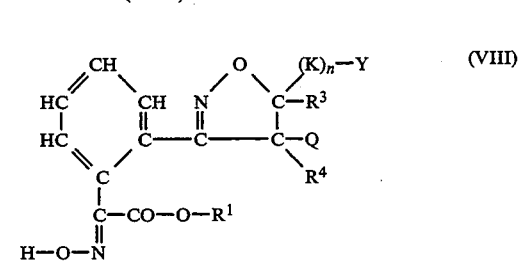
(VIII)

being obtained, which is subsequently caused to react with a halogenating agent $R^2$—X in which $R^2$ and X have the same meaning as disclosed above, under analogous conditions to as disclosed above for the conversion of the salt of general formula (VI) into the compound of formula (Ia), with the compound of general formula (Ib):

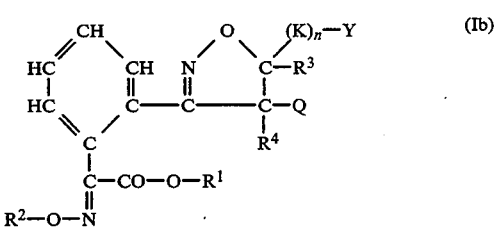
(Ib)

being obtained.

The compounds of general formula (II) can be prepared by means of the action of a compound of general formula (IX):

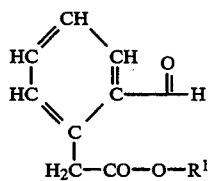

(IX)

wherein $R^1$ has the same meaning as disclosed hereinabove, with a hydroxylamine hydrochloride in the presence of a base such as, e.g., sodium bicarbonate, sodium carbonate, triethylamine.

The compounds of general formula (IX) can be prepared by condensation of sodium methyl malonate anion with o-bromobenzaldehyde according to such synthesis methodologies as disclosed in technical literature, such as, e.g., in Setsune et al., Chemistry Letters, pages 367–370 (1981).

The compounds of general formula (III) can be obtained according to methods known from technical literature, such as, e.g., in J. March, Advanced Organic Chemistry, II Ed., Int. St. Edition.

The compounds of general formula (I) display a particular high fungicidal activity against phytopathogenic fungi which attack grape vines, sugar beet, cereal, Cucurbits crops and fruit-trees.

They display both preventative and curative activities when are applied to useful plants or parts thereof, such as, e.g., leaves, and result to be particularly effective in preventing the illnesses caused by obliged pathogenic fungi such as, e.g., those belonging to *Erysiphe* and *Helminthosporium* genera.

The plant diseases which can be combatted with the compounds according to the present invention are, e.g., the following:

*Helminthosporium teres* on cereals;
*Erysiphe graminis* on cereals;
*Puccinia spp.* on cereals;
*Plasmopara viticola* on grape vines;
*Phytium* on horticultural crops;
*Phytophthora spp.* on horticultural crops;
*Septoria spp.* on cereals;
*Sphaerotheca fuliginea* on Cucurbits (e.g., cucumber);
*Rhyncosporium* on cereals;
*Podosphaera leucotricha* on apple tree;
*Uncinula necator* on grape vines;
*Venturia spp.* on fruit-trees;
*Pyricularia oryzae* on rice;
*Botrytis cinerea;*
*Fusarium spp.* on cereals;
and so forth.

Besides performing a fungicidal action of both curative and preventative character, as disclosed above, the compounds of general formula (I) display an either low or null phytotoxicity.

For practical uses in agriculture, having available fungicidal compositions containing, as their active substance, one or more compounds of general formula (I), possibly also as an isomer mixture, is often useful.

These compositions may be applied to any parts of the plant, e.g., on leaves, stems, branches and roots, or to the same seeds, before sowing, or, also on the soil on which the plant grows.

Compositions can be used, which are in the form of dry dusts, wettable dusts, emulsifiable concentrates, microemulsions, pastes, granulates, solutions, suspensions, and so forth: the selection of the type of composition will depend on the specific use.

The compositions are prepared according to known methodologies, e.g., by diluting or dissolving the active substance with a solvent means and/or a solid diluent, possibly in the presence of surfactants.

As solid diluents, or carriers, the following can be used: silica, China clay, bentonite, talc, fossil meal, dolomite, calcium carbonate, magnesia, gypsum, clays, synthetic silicates, actapulgite, sepiolite.

As liquid extenders, besides, of course, water, various solvent types can be used, such as, e.g., aromatic solvents (xylenes or blends of alkylbenzenes); chlorinated aromatic solvents (chlorobenzene); paraffins (petroleum fractions); alcohols (methanol, propanol, butanol, octanol, glycerol); amines; amides (N,N'-dimethylformamide, N-methylpyrrolidone); ketones (acetone, cyclohexanone, acetophenone, isophorone, ethyl amyl ketone); esters (isobutyl acetate).

As surfactants, sodium, calcium, triethanolamine salts of alkyl sulfates, alkyl aryl sulfonates, polyethoxylated alkyl phenols, fatty alcohol condensates with ethylene oxide, polyethoxylated fatty acids, polyethoxylated sorbitol esters, lignosulfonates.

The compositions can also contain special additives for particular purposes, such as, e.g., adhesive agents, such as gum arabic, polyvinyl alcohol, polyvinylpyrrolidone.

If so desired, to the compositions according to the present invention also other compatible active substances such as fungicides, phytoregulants, antibiotics, herbicides, insecticides, fertilizers, can be added.

The concentration of active substance in the above said compositions may vary within a wide range, according to the active compound, crop, pathogen, environmental conditions, and adopted formulation type.

In general, the concentration of the active substance is comprised within the range of from 0.1 to 95%, preferably of from 0.5 to 90%.

The following examples are reported for merely illustrative purposes, and are not limitative of the scope of the invention.

EXAMPLE 1

Preparation of (Z)-methyl 3-methoxy-2-}2-[5-(4-chlorophenyl)isooxazol-3-yl]phenyl}acrilate (Compound No. 1)

Under a nitrogen atmosphere, 0.32 g of sodium hydride at 80% (w/w) in paraffin is dispersed in 10 cm³ of anhydrous dimethylformamide.

Then 1.5 g of methyl 2-{2-[5-(4-chlorophenyl)isooxazol-3-yl]phenyl}acetate in 7 cm³ of methyl formate and 10 cm³ of anhydrous dimethylformamide are added dropwise during 30 minutes.

The mixture is kept heated at 45° C. during 6 hours.

The reaction mixture is cooled down to 5° C. and 3.5 cm³ of methyl iodide (CH₃I) is added.

The resulting solution is kept standing overnight at room temperature, and then is diluted with water and is extracted with ethyl acetate.

The organic phase is washed with brine, is thoroughly desiccated over sodium sulfate, and is concentrated under reduced pressure.

The resulting raw material is purified by silica gel chromatography, eluting with 8:2 hexane:ethyl acetate.

An amount of 0.85 g of Compound No. 1 is obtained in a yield of 50.2%; the structure of this compound is reported in Table 1.

The N.M.R. spectroscopic data is reported in Table 2.

EXAMPLE 2

Preparation of (Z)-methyl 2-methoxyimino-2-{2-[5-(4-chlorophenyl)isooxazol-3-yl]phenyl}acetate (Compound No. 2)

Under a nitrogen atmosphere, 0.35 g of sodium hydride at 80% (w/w) in paraffin is dispersed in 10 cm³ of anhydrous dioxane.

Then 1.5 g of methyl 2-{2-[5-(4-chlorophenyl)isooxazol-3-yl]phenyl}acetate in 15 cm³ of amyl nitrite and 10 cm³ of anhydrous dioxane are added dropwise during 30 minutes.

The mixture is kept 48 hours at room temperature, and is subsequently kept heated at 40° C. during 4 hours.

The reaction mixture is cooled down to 5° C. and 3.5 cm3 of methyl iodide (CH₃I) is added.

The resulting solution is kept standing overnight at room temperature, and then is diluted with water and extracted with ethyl acetate.

The organic phase is washed with brine, is thoroughly desiccated over sodium sulfate, and is concentrated under reduced pressure.

The resulting raw material is purified by silica gel chromatography, eluting with 8:2 hexane:ethyl acetate.

An amount of 0.45 g of Compound No. 2 is obtained in a yield of 26.5%; the structure of this compound is reported in Table 1.

The N.M.R. spectroscopic data is reported in Table 2.

EXAMPLES 3-21

By operating according to the same procedure as of Examples 1 and 2, the Compound Nos. 3-21, the structures of which are reported in Table 1 were prepared.

The respective N.M.R. spectroscopic data are reported in Table 2.

EXAMPLE 22

Determination of the preventative fungicidal activity against Cucurbits powdery mildew (*Sphaerotheca fuliginea*)

Leaves of cucumber plants Marketer cultivar, grown in pots in a conditioned environment (20±1° C., 70% R.H.), were treated by spraying both of their leaf faces with the Compound Nos. 1-21 in water:acetone solution at 20% acetone by volume.

After a 24-hour stay in the conditioned environment, the leaves of the plants were sprayed on both of their faces with an aqueous suspension of conidia of *Sphaerotheca fuliginea* (200,000 conidia per cm³).

The plants were kept in a humidity-saturated environment, at 21° C., during the fungus incubation period.

At the end of said time period (8 days), the fungicidal activity of the compounds was evaluated according to a percent rating scale ranging from 100 (healthy plant) to 0 (completely infected plant).

All said Compound Nos. 1-21 received a control rating higher than 90, at the concentration of 500 ppm.

EXAMPLE 23

Determination of the preventative fungicidal activity against net blotch of barley (*Helminthosporium teres*)

Leaves of barley plants Arna cultivar, grown in pots in a conditioned environment (20±1° C., 70% R.H.), were treated by spraying both of their Leaf faces with the Compound Nos, 1-21 in water:acetone solution at 20% acetone by volume.

After a 24-hour stay in the conditioned environment, the leaves of the plants were sprayed on both of their faces with an aqueous suspension of conidia of *Helminthosporium teres* (250,000 conidia per cm³).

The plants were kept in a humidity-saturated environment, at 21° C., during the fungus incubation period.

At the end of said time period (12 days), the fungicidal activity of the compounds was evaluated according to a percent rating scale ranging from 100 (healthy plant) to 0 (completely infected plant).

All said Compound Nos. 1-21 received a control rating higher than 90, at the concentration of 500 ppm.

EXAMPLE 24

Determination of the preventative fungicidal activity against downy mildew on grape vines (*Plasmopara viticola*)

Leaves of grape vine plants Dolcetto cultivar, grown in pots in a conditioned environment (20±1° C., 70% R.H.), were treated by spraying both of their leaf faces with the Compound Nos. 1-21 in water:acetone solution at 20% acetone by volume.

After a 24-hour stay in the conditioned environment, the leaves of the plants were sprayed on both of their faces with an aqueous suspension of conidia of *Plasmopara viticola* (200,000 conidia per cm³).

The plants were kept in a humidity-saturated environment, at 21° C., during the fungus incubation period.

At the end of said time period (7 days), the fungicidal activity of the compounds was evaluated according to a percent rating scale ranging from 100 (healthy plant) to 0 (completely infected plant).

All said Compound Nos. 1-21 received a control rating higher than 90, at the concentration of 500 ppm.

TABLE 1

Compound No. 1

(Z)-methyl 3-methoxy-2-{2-[5-(4-chlorophenyl)-isooxazol- 3-yl]phenyl}acrylate.

Compound No. 2

(Z)-methyl 2-methoxyimino-2-{2-[5-(4-chlorophenyl)isooxazol-3-yl]phenyl}acetate.

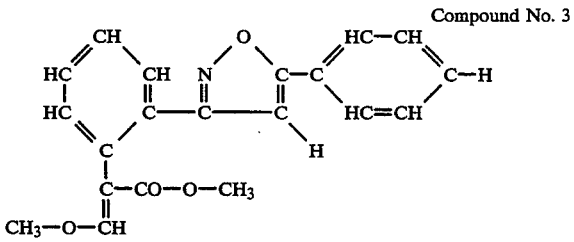

(Z)-methyl 3-methoxy-2-[2-(5-phenyl)-isooxazol-3-yl]phenyl}acrylate.

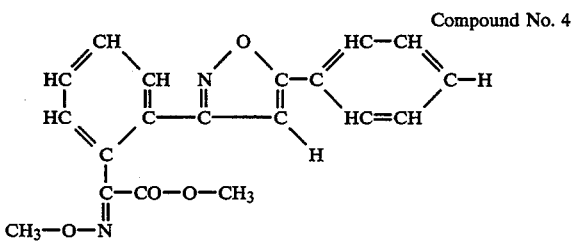

(Z)-methyl 2-methoxyimino-2-[2-(5-phenyl)isooxazol-3-yl]phenylacetate.

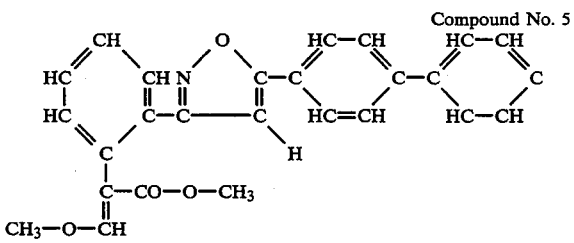

(Z)-methyl 3-methoxy-2-{2-[5-(4-phenylphenyl)-isooxazol-3-yl]phenyl}acrylate.

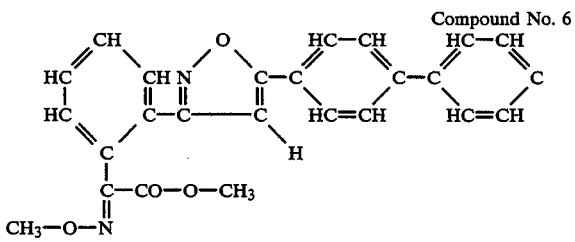

(Z)-methyl 2-methoxyimino-2-{2-[5-(4-phenylphenyl)isooxazol-3-yl]phenyl}acetate;
and furthermore, the following compounds:
Compound No. 7
(E)-methyl 3-methoxy-2-{2-[5-(4-methoxyphenyl)-isooxazol-3-yl]phenyl}acrylate
Compound No. 8
(E)-methyl 3-methoxy-2-{2-[5-(4-methylphenyl)-isooxazol-3-yl]phenyl}acrylate
Compound No. 9
(E) -methyl 3-methoxy-2-{2-[5-(4-tert.-butylphenyl-)isooxazol-3-yl]phenyl}acrylate
Compound No. 10
(E)-methyl 3-methoxy-2-{2-[5-(4-trifluoromethylphenyl)-isooxazol-3-yl3phenyl}acrylate
Compound No. 11
(E)-methyl 3-methoxy-2-{2-[5-(3,4-dimethoxyphenyl-)isooxazol-3-yl]phenyl}acrylate
Compound No. 12
(E)-methyl 3-methoxy-2-{2-[5-(2-methylphenyl)-isooxazol-3-yl]phenyl}acrylate
Compound No. 13
(E)-methyl 3-methoxy-2-{2-[5-(2-chlorophenoxymethyl)isooxazol-3-yl]phenyl}acrylate
Compound No. 14
(E)-methyl 3-methoxy-2-{2-[5-(2-methylphenoxymethyl)isooxazol-3-yl]phenyl}acrylate
Compound No. 15
(E)-methyl 3-methoxy-2-{2-[5-(4-cyanophenyl)-isooxazol-3-yl]phenyl}acrylate
Compound No. 16
(E)-methyl 3-methoxy-2-{2-[5-(4-(2-trifluoromethoxy-1,1,2-trifluoroethoxy)phenyl)-isooxazol-3-yl]-phenyl}acrilate
Compound No. 17
(E)-methyl 3-methoxy-2-{2-[5-(2-cyanophenyl)isooxazol-3-yl]phenyl}acrylate
Compound No. 18
(E)-methyl 3-methoxy-2-{2-[5-(2-fluorophenyl)-isooxazol-3-yl]phenyl}acrylate
Compound No. 19
(E)-methyl 3-methoxy-2-{2-[5-(2-chlorophenyl-)isooxazol-3-yl]phenyl}acrylate
Compound No. 20
(E)-methyl 3-methoxy-2-[2-(5-tert.-butyl-isooxazol-3-yl)phenyl]acrylate
Compound No. 21
(E)-methyl 3-methoxy-2-{2-[5-(4-chlorophenyl-)isooxazol-3-yl]phenyl}acrylate

TABLE 2

| Compound | Spectroscopic data from 60 NHz N.M.R. (DMSO-d6) |
|---|---|
| 1 | 7.81–7.36 m (9H), 6.60 s (1H), 3.76 s (3H), 3.59 s (3H) |
| 2 | 7.84–7.30 m (8H), 6.58 s (1H), 4.00 s (3H), 3.60 s (3H) |
| 3 | 7.75–7.34 m (8H), 6.61 s (1H), 3.78 s (3H), 3.60 s (3H) |
| 4 | 7.70–7.32 m (7H), 6.62 s (1H), 3.99 s (3H), 3.59 s (3H) |
| 5 | 6.95–7.26 m (14H), 6.61 s (1H), 3.77 s (3H), 3.61 s (3H) |
| 6 | 7.01–7.30 m (13H), 6.58 s (1H), 4.01 s (3H), 3,59 s (3H) |
| 7 | 7.90–6.90 m (8H); 7.56 s (1H); 6.50 s (1H); 3.90 s (3H); 3.80 s (3H); 3.62 s (3H). |
| 8 | 7.80–7.23 (8H), 7.53 s (1H), 6.60 s (1H), 3.83 s (3H), 3.63 s (3H), 2.43 s (3H). |
| 9 | 7.80–7.15 m (8H), 7.47 s (1H), 6.52 s (1H), 3.73 s (3H), 3.60 s (3H), 1.33 s (9H). |
| 10 | 7.95–7.15 m (8H), 7.45 s (1H), 6.60 s (1H), 3.74 s (3H), 3.57 s (3H). |
| 11 | 7.83–6.75 m (9H), 6.48 s (1H), 3.93 s (3H), 3.90 s (3H), 3.72 s (3H), 3.60 s (3H) . |
| 12 | 7.92–7.10 m (9H) 6.55 s (1H), 3.70 s (3H), 3.56 s (3H), 2.50 s (3H). |
| 13 | 7.80–6.82 m (9H), 6.47 s (1H), 5.25 s (2H), 3.71 s (3H), 3.60 s (3H). |
| 14 | 7.82–6.70 m (9H) 6.44 s (1H), 5.15 s (2H), 3.63 s (3H), 3.57 s (3H), 2.22 s (3H). |
| 15 | 7.85–6.90 m (9H), 6.70 s (1H), 3.77 s (3H), 3.57 s (3H). |
| 16 | 7.95–6.85 m (8H), 7.42 s (1H), 6.52 s (1H), 5.87 dt (1H), 3.70 s (3H), 3.53 s (3H). |

TABLE 2-continued

| Compound | Spectroscopic data from 60 NHz N.M.R. (DMSO-d6) |
|---|---|
| 17 | 8.20–7.25 m (8H), 7.62 s (1H), 7.30 s (1H), 3.80 s (3H), 3.65 s (3H). |
| 18 | 8.10–7.00 m (8H), 7.50 s (1H), 6.80 d (1H), 3.70 s (3H), 3.57 s (3H). |
| 19 | 8.10–7.20 m (8H), 7.60 s (1H), 7.10 s (1H), 3.76 s (3H), 3.65 s (3H).. |
| 20 | 7.85–7.28 m (4H). 7.53 s (1H), 6.05 s (1H), 3.72 s (3H), 3.57 s (3H), 1.40 s (9H). |
| 21 | 7.95–7.30 m (9H), 6.70 s (1H), 3.86 s (3H), 3.63 s (3H). |

We claim:

1. Compounds of arylacetic esters having the general formula (I):

in which:

$R^1$ and $R^2$, which may be the same or different from each other, represent an either linear or branched $C_1$–$C_6$ alkyl or haloalkyl group;

$R^3$ and $R^4$, which may be the same or different from each other, represent a hydrogen atom, a $C_1$–$C_2$ alkyl group, a $COOR^5$ group in which $R^5$ represents an either linear or branched $C_1$–$C_6$ alkyl group, a cyano group, or, taken together, constitute a bond;

W represents a nitrogen atom, or the $$=\overset{|}{C}-H$$

group;

Y and Q, which may be the same or different from each other, represent a nitrile group, an either linear or branched $C_1$–$C_6$ alkyl or carboalkoxy group, a phenyl group, a heterocyclic $C_5$–$C_{10}$ group in which the heteroatoms are selected from oxygen, nitrogen or sulfur, wherein said phenyl, heterocyclic, linear or branched $C_1$–$C_6$ alkyl or alkoxy groups may also be optionally substituted with:

halogens, such as chloro, fluoro, bromo, iodo;

linear or branched $C_1$–$C_6$ alkyl or haloalkyl groups;

linear or branched $C_1$–$C_6$ alkoxy or haloalkoxy groups;

a nitrile group;

an either linear or branched $C_2$–$C_8$ carboxyalkyl group;

a —(V)$_m$—Z group, in which Z stands for:

an either linear or branched $C_1$–$C_6$ alkyl group, a phenyl group, a heterocyclic $C_5$–$C_{10}$ group in which the heteroatoms are selected from oxygen, nitrogen or sulfur, wherein said phenyl, heterocyclic, linear or branched $C_1$–$C_6$ alkyl groups may also be optionally substituted with:

halogens, such as chloro, fluoro, bromo, iodo;

linear or branched $C_1$–$C_6$ alkyl or haloalkyl groups;

linear or branched $C_1$–$C_6$ alkoxy or haloalkoxy groups;

a nitrile group;

an either linear or branched $C_2$–$C_8$ carboxyalkyl group;

K and V, which may be the same or different from each other, represent an oxygen or sulfur atom, or a carbonyl group;

n and m, which may be the same or different from each other, are zero, or 1.

2. Antifungal agents for agricultural purposes, constituted by compounds of arylacetic esters having the general formula (I):

in which:

$R^1$ and $R^2$, which may be the same or different from each other, represent an either linear or branched $C_1$–$C_6$ alkyl or haloalkyl group;

$R^3$ and $R^4$, which may be the same or different from each other, represent a hydrogen atom, a $C_1$–$C_2$ alkyl group, a $COOR^5$ group in which $R^5$ represents an either linear or branched $C_1$–$C_6$ alkyl group, a cyano group, or, taken together, constitute a bond;

W represents a nitrogen atom, or the $$=\overset{|}{C}-H$$

group;

Y and Q, which may be the same or different from each other, represent a nitrile group, an either linear or branched $C_1$–$C_6$ alkyl or carboalkoxy group, a phenyl group, a heterocyclic $C_5$–$C_{10}$ group in which the heteroatoms are selected from oxygen, nitrogen or sulfur, wherein said phenyl, heterocyclic, linear or branched $C_1$–$C_6$ alkyl or alkoxy groups may also be optionally substituted with:

halogens, such as chloro, fluoro, bromo, iodo;

linear or branched $C_1$–$C_6$ alkyl or haloalkyl groups;

linear or branched $C_1$–$C_6$ alkoxy or haloalkoxy groups;

a nitrile group;

an either linear or branched $C_2$–$C_8$ carboxyalkyl group;

a —(V)$_m$—Z group, in which Z stands for:

an either linear or branched $C_1$–$C_6$ alkyl group, a phenyl group, a heterocyclic $C_5$–$C_{10}$ group in which the heteroatoms are selected from oxygen, nitrogen or sulfur, wherein said phenyl, heterocyclic, linear or branched $C_1$–$C_6$ alkyl groups may also be optionally substituted with:

halogens, such as chloro, fluoro, bromo, iodo;

linear or branched $C_1$–$C_6$ alkyl or haloalkyl groups;

linear or branched $C_1$–$C_6$ alkoxy or haloalkoxy groups;

a nitrile group;

an either linear or branched $C_2$–$C_8$ carboxyalkyl group;

K and V, which may be the same or different from each other, represent an oxygen or sulfur atom, or a carbonyl group;

n and m, which may be the same or different from each other, are zero, or 1.

3. Antifungal agents for agricultural purposes according to claim 2, in which $R^1$ and $R^2$ are: methyl, ethyl, trifluoromethyl, 1,1,2,2-tetrafluoroethyl.

4. Antifungal agents for agricultural purposes according to claim 2, in which $R^3$ and $R^4$ are: methyl, ethyl, carbomethoxy, carboethoxy, carboisopropoxy.

5. Antifungal agents for agricultural purposes according to claim 2, in which Y, Q and Z are: methyl, ethyl, isopropyl, tert.-butyl, trifluoromethyl, perfluoroethyl, 1,1,2,2-tetrafluoroethyl, phenyl, 2-chlorophenyl, 3-chlorophenyl, 4-chlorophenyl, 2,4-dichlorophenyl, 4-fluorophenyl, 3-methoxyphenyl, 3-trifluoromethylphenyl, 4-trifluoromethylphenyl, 3-trifluoromethoxyphenyl, 2-cyanophenyl, 4-cyanomethyl, 2-carbomethoxyphenyl, pyridyl, 3-cyanopyridyl, 4-cyanopyridyl, 3-carbomethoxypyridyl, 3,5-dichloropyridyl, pyrimidyl, 4-methylpyrimidyl, 2-trifluoromethylpyrimidyl, 4-trifluoromethylpyrimidyl, pyradizinyl, 2-trifluoro-methylpyradizinyl, 5-methylthienyl, 5-trifluoromethyl-thienyl, 4-methyl-5-trifluoromethylthiazolyl, 5-tert.-butylthiazolyl, 5-chlorobenzothiazolyl.

6. Antifungal agent for agricultural purposes according to claim 2, constituted by (Z)-methyl 3-methoxy-2-{2-[5-(4-chlorophenyl)-isooxazol-3-yl]-phenyl}acrylate.

7. Antifungal agent for agricultural purposes according to claim 2, constituted by (Z)-methyl 2-methoxyimino-2-{2-[5-(4-chlorophenyl)-isooxazol-3-yl]phenyl}acetate.

8. Antifungal agent for agricultural purposes according to claim 2, constituted by (Z)-methyl 3-methoxy-2-[2-(5-phenyl)-isooxazol-3-yl]phenyl}-acrylate.

9. Antifungal agent for agricultural purposes according to claim 2, constituted by (Z)-methyl 2-methoxyimino-2-[2-(5-phenyl)isooxazol-3-yl]phenylacetate.

10. Antifungal agent for agricultural purposes according to claim 2, constituted by (Z)-methyl 3-methoxy-2-{2-[5-(4-phenylphenyl)isooxazol-3-yl]phenyl}acrylate.

11. Antifungal agent for agricultural purposes according to claim 2, constituted by (Z)-methyl 2-methoxyimino-2-{2-[5-(4-phenylphenyl)isooxazol-3-yl]phenyl}acetate.

12. Antifungal agent for agricultural purposes according to claim 2, constituted by:
(E)-methyl 33-methoxy-2-{2-[5-(4-methoxyphenyl)isooxazol-3-yl]phenyl}acrylate.

13. Antifungal agent for agricultural purposes according to claim 2, constituted by:
(E)-methyl 3-methoxy-2-{2-[5-(4-methylphenyl)isooxazol-3-yl]phenyl}acrylate.

14. Antifungal agent for agricultural purposes according to claim 2, constituted by:
(E)-methyl 3-methoxy-2-{2-[5-(4-tert.-butylphenyl)isooxazol-3-yl]phenyl}acrylate.

15. Antifungal agent for agricultural purposes according to claim 2, constituted by:
(E)-methyl 3-methoxy-2-{2-[5-(4-trifluoromethylphenyl)-isooxazol-3-yl]phenyl}acrylate, 16. Antifungal agent for agricultural purposes according to claim 2, constituted by:
(E)-methyl 3-methoxy-2-{2-[5-(3,4-dimethoxyphenyl)-isooxazol-3-yl]phenyl}acrylate.

17. Antifungal agent for agricultural purposes according to claim 2, constituted by:
(E)-methyl 3-methoxy-2-{2-[5-(2-methylphenyl)-isooxazol-3-yl]phenyl}acrylate.

18. Antifungal agent for agricultural purposes according to claim 2, constituted by:
(E)-methyl 3-methoxy-2-{2-[5-(2-chlorophenoxymethyl)-isooxazol-3-yl]phenyl}-acrylate.

19. Antifungal agent for agricultural purposes according to claim 2, constituted by:
(E)-methyl 3-methoxy-2-{2-[5-(2-methylphenoxymethyl)-isooxazol-3-yl]phenyl}-acrylate.

20. Antifungal agent for agricultural purposes according to claim 2, constituted by:
(E)-methyl 3-methoxy-2-{2-[5-(4-cyanophenyl)-isooxazol-3-yl]phenyl}acrylate.

21. Antifungal agent for agricultural purposes according to claim 2, constituted by:
(E)-methyl 3-methoxy-2-{2-[5-(4-(2-trifluoromethoxy-1,1,2-trifluoroethoxy)phenyl)-isooxazol-3-yl]phenyl}acrilate.

22. Antifungal agent for agricultural purposes according to claim 2, constituted by:
(E)-methyl 3-methoxy-2-{2-[5-(2-cyanophenyl)isooxazol-3-yl]phenyl}acrylate.

23. Antifungal agent for agricultural purposes according to claim 2, constituted by:
(E)-methyl 3-methoxy-2-{2-[5-(2-fluorophenyl)isooxazol-3-yl]phenyl}acrylate.

24. Antifungal agent for agricultural purposes according to claim 2, constituted by:
(E)-methyl 3-methoxy-2-{2-[5-(2-chlorophenyl)isooxazol-3-yl]phenyl}acrylate.

25. Antifungal agent for agricultural purposes according to claim 2, constituted by:
(E)-methyl 3-methoxy-2-[2-(5-tert.-butyl-isooxazol-3-yl)phenyl]acrylate.

26. Antifungal agent for agricultural purposes according to claim 2, constituted by:
(E)-methyl 3-methoxy-2-{2-[5-(4-chlorophenyl)isooxazol-3-yl]phenyl}acrylate.

27. Fungicidal compositions containing one or more compounds according to claim 2, either alone or in the presence of solid supports, liquid diluents, surfactants, or other active principles.

28. Method for combatting fungal infections, consisting in applying onto plants, leaves, stems, branches and roots, on to the same seeds before sowing, or to the soil on which the plant grows, fungicidal compositions according to claim 27.

* * * * *